(12) United States Patent
Greter et al.

(10) Patent No.: US 8,444,025 B2
(45) Date of Patent: May 21, 2013

(54) DISCHARGE APPARATUS COMPRISING ROTATING DEVICE

(75) Inventors: Andy Greter, Baar (CH); Samuel Kaufmann, Lucerne (CH); Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 269 days.

(21) Appl. No.: 12/812,285

(22) PCT Filed: Nov. 25, 2008

(86) PCT No.: PCT/CH2008/000498
§ 371 (c)(1),
(2), (4) Date: Jul. 9, 2010

(87) PCT Pub. No.: WO2009/086644
PCT Pub. Date: Jul. 16, 2009

(65) Prior Publication Data
US 2010/0282774 A1  Nov. 11, 2010

(30) Foreign Application Priority Data

Jan. 11, 2008  (CH) .......................................... 38/08
Jul. 31, 2008  (CH) ...................................... 1245/08

(51) Int. Cl.
*B67D 7/60* (2010.01)
*B05C 17/01* (2006.01)

(52) U.S. Cl.
USPC ............... 222/390; 222/39; 222/46; 222/137; 222/309; 222/327

(58) Field of Classification Search
USPC  222/39, 46, 137, 309, 327, 386, 390; 433/90; 401/172–175
See application file for complete search history.

(56) References Cited

U.S. PATENT DOCUMENTS 2,412,295 A * 12/1946 Shaffer, Jr. ...................... 222/26
3,815,785 A *  6/1974 Gilmont .......................... 222/46
(Continued)

FOREIGN PATENT DOCUMENTS

CN     1516625 A    7/2004
DD    213 848 A1   9/1984
(Continued)

OTHER PUBLICATIONS

Chinese Office Action corresponding to Chinese Patent Application No. 200880124476.9, dated Dec. 21, 2011.

*Primary Examiner* — Kevin P Shaver
*Assistant Examiner* — Leslie Tanner
(74) *Attorney, Agent, or Firm* — Sughrue Mion, PLLC (57) ABSTRACT

A discharge apparatus comprising at least one container (1; 101) is provided, said container receiving a component and having an outlet (2) and a discharge element (3, 103). The discharge apparatus further comprises a rotating device, which has a drive member (4; 104) and a rotating member (5; 105), wherein upon a rotation of the rotating member relative to the drive member the drive member is moved in the axial direction and drives the discharge element in the at least one container for discharging the components. A housing element (6; 106) is provided, on or in which the at least one container (1; 101), the drive member (4; 104), and the rotating member (5; 105) are disposed, wherein at least the at least one container (1; 101) can be removed or is provided in the housing element (6; 106). The rotating device, together with the housing element, forms an accessory for the container.

24 Claims, 8 Drawing Sheets

U.S. PATENT DOCUMENTS

| | | | | |
|---|---|---|---|---|
| 4,260,076 A | * | 4/1981 | Bergman | 222/46 |
| 4,429,724 A | * | 2/1984 | Dorros et al. | 141/27 |
| 4,479,781 A | * | 10/1984 | Herold et al. | 433/90 |
| 4,485,944 A | | 12/1984 | Eichholz | |
| 4,595,124 A | * | 6/1986 | Duval et al. | 222/39 |
| 4,623,337 A | | 11/1986 | Maurice | |
| 4,813,870 A | | 3/1989 | Pitzen et al. | |
| 4,913,553 A | | 4/1990 | Falco | |
| 5,104,005 A | | 4/1992 | Schneider, Jr. et al. | |
| 5,304,152 A | * | 4/1994 | Sams | 604/207 |
| 6,047,861 A | * | 4/2000 | Vidal et al. | 222/137 |
| 6,347,728 B1 | * | 2/2002 | Apolloni et al. | 222/320 |
| 6,520,381 B1 | | 2/2003 | Prestele | |
| 7,086,564 B1 | * | 8/2006 | Corrigan | 222/39 |
| 7,954,672 B2 | * | 6/2011 | Keller | 222/137 |
| 2004/0216591 A1 | | 11/2004 | Assadi et al. | |
| 2007/0072146 A1 | | 3/2007 | Pierson | |

FOREIGN PATENT DOCUMENTS

| | | |
|---|---|---|
| GB | 2 011 550 A | 7/1979 |
| WO | 2007/041266 A1 | 4/2007 |
| WO | 2008/009143 A1 | 1/2008 |

* cited by examiner

DISCHARGE APPARATUS COMPRISING ROTATING DEVICE

The present invention relates to a discharge apparatus for dosing and discharging a component from at least one container, in particular a discharge apparatus that is suitable for mixing at least two components. The invention further relates to a system for dosing and discharging a component from at least one container.

PRIOR ART

In various technical fields, and also in medicine, it is necessary for a product, for example a medical or pharmaceutical product, to be discharged with exact dosing from the container in which it is stored. The products are often supplied in syringes with a container for the product, which container has an outlet, and with a piston rod which, with a stopper, seals the container in a leaktight manner. Pressing the piston rod in by hand results in the product being discharged from the container through the outlet. This type of discharging does not permit precise dosing. It is therefore inaccurate and is associated with errors. U.S. Pat. No. 4,479,781 discloses a discharge appliance for the metered discharging of a product from a syringe, in which an accessory is used to permit exact dosing. The accessory for this purpose has a grip with two forks, between which a syringe can be fitted. The piston rod is held in a rotationally fixed manner by one fork, and the syringe container can be rotated within the second fork relative to the piston rod. The product is in this way discharged.

It is also necessary, in many technical fields, for a mixture to be mixed only shortly before its use or administration. For this purpose, the prior art discloses various discharge apparatuses or mixing apparatuses that have at least two containers with different components and that can discharge the various components simultaneously from their respective container. The containers are mostly present in the form of syringes or carpules, which have an outlet at one end and, at the other end, a discharge piston for example. The respective component is received in the interior of the syringe and can be ejected through the outlet by an advance movement of the discharge piston. The discharge piston can be adjoined by a piston rod, with which the discharge piston can be pushed forward inside the syringe. To be able to discharge two components simultaneously and mix them with each other, the syringes are inserted parallel to each other into a housing, and the piston rods are pushed forward simultaneously in the respective syringe by a drive mechanism. The different components from the two syringes are ejected through the respective outlet and, for example, dispensed into a common container. It is also possible for a mixer attachment to be fitted onto the two outlets of the discharge apparatus, which mixer attachment has a mixing chamber with mixing elements for mixing the two components, and the mixed product is then dispensed from the mixer attachment.

WO 2007/041266A1 discloses, for example, a dispensing syringe with several containers for dispensing a mixture for dentistry. The dispensing syringe has a syringe body in which two containers, each holding one component, are accommodated parallel to each other. A piston rod is also provided, which is divided in two so as to give two interconnected rods which are arranged parallel to each other and which each protrude into a container of the syringe body. On the outer surface, the two rods have an outer thread. A rotary sleeve, which is rotatable about the syringe body but is not axially movable, is provided on one end of the syringe body. The rotary sleeve has an inner thread, which interacts with the outer thread of the piston rod. In order to discharge the two components simultaneously from their containers, the rotary sleeve is turned relative to the syringe body and to the piston rod. The piston rod, by virtue of its threaded connection to the rotary sleeve, is pushed in the axial direction into the containers and thus discharges the component from the containers. After the piston rod has been pushed fully into the containers, the dispensing syringe is discarded. There is no provision for re-use of the syringe or for replacement of individual structural elements of the syringe.

WO 2008/009143 discloses a dispensing appliance for a multiple container, comprising a housing for the multiple container, on which housing a rotary part is provided. Between the housing and the rotary part, a thread is provided to allow the housing to be screwed into the rotary part. For this purpose, the rotary part has two concentric sleeves, the inner sleeve having an outer thread. The inner circumference of the housing has an inner thread, which cooperates with the outer thread of the inner sleeve of the rotary part. When the rotary part is turned relative to the housing, the housing wall is screwed in between the two sleeves of the rotary part, and the inner sleeve acts as discharge piston on the piston rods of the two containers in the interior of the housing, such that the components thereof are ejected simultaneously. Once the rotary part has been screwed fully over the housing, the components have been discharged, and the dispensing appliance is discarded. There is no provision for using the dispensing appliance a second time for further containers.

It is therefore an object of the present invention to make available a discharge apparatus for discharging components from at least one container, which discharge apparatus can be re-used, can be adapted to specific discharge requirements, in particular dosing requirements, is suitable for discharging from different container types, is made up of a small number of structural parts, is easy to clean and to sterilize, and permits simple handling during discharge. It is in particular an object of the invention to provide a system for discharging components from containers, which system comprises a discharge device, which can be used for different containers and which is provided as a kind of accessory for the different component containers.

SUMMARY OF THE INVENTION

A discharge apparatus according to the present invention has at least one container that can receive a component and has an outlet and a discharge element. The discharge apparatus preferably comprises two or more containers that each receive a component and each have an outlet and a discharge element. The containers are preferably designed in the manner of a syringe that comprises a sleeve-shaped body, with an outlet at one end and with a piston or stopper at the opposite end, and a piston rod for pushing the piston forward. In principle, however, it is also possible to use other forms of containers, for example ampules or cartridges, or also a flexible container in the manner of a pouch. Moreover, the discharge apparatus according to the present invention has a rotating device that comprises a drive member and a rotary member, wherein, upon a rotation of the rotary member relative to the drive member, the drive member is movable in the axial direction relative to the rotary member and drives the discharge elements in the at least two containers for discharging the components. For this purpose, the rotating device preferably has a threaded connection between the drive member and the rotary member. The threaded connection can preferably be provided directly between the drive member and the rotary member. However, it is also possible to provide the threaded connection between drive member and rotary member via further thread elements, for example as in a gear system, if appropriate also with step-up or step-down. For example, step-up can be advantageous if, when discharging the components or when mixing the components, it is necessary to ensure particularly slow discharge. In an advantageous embodiment of the threaded connection, the drive member is provided as a threaded rod, which interacts with a thread on the rotary member. The threaded rod engages directly on the discharge elements of the containers or acts indirectly on the discharge elements via further structural parts.

According to the present invention, the discharge apparatus is provided with a housing element, on or in which the at least two containers, the drive member and the rotary member are disposed, wherein the container or at least one of the containers is mounted removably on or in the housing element. In the case of several containers, these are arranged on or in the housing element in such a way that their respective outlets and their discharge elements point in the same direction. For example, syringe-like containers can be arranged in parallel alongside one another. The several containers are advantageously arranged in a triangular, square or ring shape. The containers can be received completely by the housing element, or they can fit only partially into the interior of the housing. Moreover, it is also possible to accommodate the containers in a second housing element and to connect the second housing element to the first housing element. It is essential in this case that the drive member can act on the discharge elements of the containers. The drive member is therefore provided in the housing element in such a way that it acts directly or indirectly on the discharge elements of the containers.

It is an advantage of the discharge apparatus according to the present invention that the rotating device with the housing element can be used several times for different containers. It is not necessary to discard the entire discharge apparatus simply because one or more containers are empty. The discharge apparatus can therefore be produced cost-effectively, and the re-used structural parts can be produced with greater quality, since the additional costs are worth while in light of said parts being re-usable. It is particularly advantageous that different containers, for example of different diameter or different length, can be inserted into the housing element. The discharge apparatus according to the invention also permits precise manual dosing of the components from the containers.

In a preferred embodiment of the present invention, it is not only the containers that can be mounted on or in the housing element in such a way as to be removable or replaceable, the drive member and/or the rotary member can also be provided removably on or in the housing element. It is thus possible to dismantle the discharge apparatus according to the present invention into its small number of structural parts and to easily clean it and autoclave it and thus prepare it for renewed use. The discharge apparatus particularly preferably has no more than the following structural parts: containers, a housing element, a drive member, and a rotary member. In addition to these structural parts, it is of course also possible to fit a discharge cannula, a mixer attachment or the like onto the outlets of the containers.

In one embodiment of the present invention, the threaded rod has a guide means that interacts with a complementary guide means on the housing element in such a way that the threaded rod is axially movable but rotationally fixed in relation to the housing element. For this purpose, the threaded rod is flattened, for example on two opposite longitudinal sides, such that two parallel guide surfaces are formed along the axis. The thread segments for the threaded connection to the rotary member are arranged between these surfaces. The housing element has, as a guide means complementing the guide surfaces, two mutually parallel flanks whose distance apart corresponds to the thickness of the threaded rod between the guide surfaces. To be able to insert the threaded rod into the housing element, it is pushed with its guide surfaces between the guide flanks. The threaded rod can thus be moved in the axial direction between the guide flanks of the housing element but, because of the abutment of the guide surfaces on the guide flanks, is prevented from rotating relative to the housing element.

The housing element receives the rotary member in such a way that the latter is rotatable relative to the housing element but is fixed in the axial direction. The rotary member is arranged on the housing in such a way that a sufficient portion extends from the housing or protrudes beyond the housing to be able to grip the rotary member and turn it relative to the housing element. In the case of a threaded rod with guide surfaces, the rotary member is arranged on the housing element in such a way that the threaded rod can be inserted or protrude into the interior of the rotary member. The rotary member is preferably sleeve-shaped and has, on its inner circumference, an inner thread that cooperates with the outer thread of the threaded rod.

To receive the rotary member, the housing element can have an annular groove about at least part of its circumference. The annular groove preferably extends through approximately 180° about the circumference of the housing element. The annular groove can be provided externally in the circumferential surface or can be provided as a kind of blind groove on an inner circumferential surface. The rotary member has a flange that fits the annular groove and that can be inserted into the annular groove. The flange is either pushed over the outer circumference of the housing element into the annular groove or is inserted along the blind groove into an inner annular groove.

To assemble the rotating device of the discharge apparatus according to the invention, the rotary member is first mounted on the housing element in such a way that the inner thread comes to lie in the axial continuation of the guide means of the housing element. Moreover, the drive member is inserted into the guide means of the housing element until it reaches the rotary member. It is inserted until the threads of the threaded connection are able to engage in one another. The rotary member is then turned relative to the housing element and to the drive member in such a way that the drive member is inserted or screwed further into the rotary member by means of the threaded connection. The housing element with the inserted rotary member and drive member forms the rotating device as an accessory for the container or containers, so as to be able to discharge the components.

To discharge the components from the container or from the several containers according to a desired dosing scheme, the containers are likewise arranged on the housing element. They are mounted in such a way that their discharge elements come to lie opposite the end of the drive member protruding from the rotary member. The containers are secured by the housing element so as to be immovable in the axial direction. The containers are also advantageously fixed in rotation, although this is not absolutely necessary for the function of the present invention. For this purpose, for example, the housing element can be provided with one or more retaining depressions, e.g., in the form of two slits, into which one or more projections, e.g. in the form of two wings, provided on the container can engage. The discharge elements of the containers, which elements are preferably designed as piston rods, can extend into the interior of the housing element, in particular also between the guide means of the latter. In this way, they come to lie opposite the drive member and can likewise be guided in the axial direction. This avoids the discharge elements jamming during their advance by the drive member.

To discharge the components from the container, the rotary member is now turned in the opposite direction, such that the drive member is pushed out of the interior of the rotary member and is guided and advanced in the axial direction by the guide means on the drive member and housing element. By being pushed forward, it strikes the discharge elements and pushes these forward simultaneously and at the same speed inside the containers. By means of the forward movement, the components are ejected in a dosed amount through the outlets.

The overall structural length of the discharge apparatus does not therefore change during the discharging procedure, which makes the apparatus easy to handle. A user simply has to insert the container or containers into a ready-to-use accessory rotating device and turn the portion of the rotary member protruding from the housing element. The turning can be done with just one hand or can be assisted by the other hand.

The discharge apparatus according to the invention is particularly advantageous for individual containers that can be inserted independently of one another into the accessory rotating device and can be individually replaced. However, it is of course also possible to use double containers, for example with one connected discharge element that acts on both containers.

In another embodiment, the rotary member can have a rotation scale on its outer surface along its circumferential direction, and the housing element has a pointer lying opposite the rotation scale. When the rotary member is turned relative to the housing, a rotation position on the rotation scale can be indicated by the pointer. The rotation scale can be provided by simple lines, by numbers or also by a color marking.

The discharge apparatus can also have a device for generating an acoustic or tactile signal upon rotation of the rotary member. For this purpose, for example, a flexible tongue protruding in the direction of the rotary member, or a flexible projection, can be provided on the housing element or mounted thereon. The rotary member can for its part be provided with a projection which, upon rotation of the rotary member, deflects the flexible tongue and, upon further rotation, frees the tongue again, such that the tongue, for example, strikes against an abutment part and thus generates a sound. It is possible in principle to provide several projections on the rotary member or also to arrange several flexible tongues on the housing element. Moreover, the flexible tongues can also be arranged on the rotary member, and the projections on the housing element. By means of such an acoustic device, the number of rotations or partial rotations can thus be indicated by means of a sound. The device can also be used as a tactile signal emitter. When the flexible tongue is deflected, the rotation of the rotary element is made slightly but perceptibly more difficult. As soon as the flexible tongue is freed again, rotating is made easier again. A user can thus also feel the number of rotations or partial rotations.

As has already been described, the housing element can be connected to a further housing element of the discharge apparatus and can be removeable therefrom. A further housing element can be advantageous, for example, for accommodating several containers. The further housing element can then be fitted on the accessory rotating device in order to dispense the components from the several containers simultaneously and in parallel according to a desired dosing scheme.

Moreover, it is also possible for the housing element to be designed in several parts, in which case the housing parts are separable from each other at least partially or at least in some places. A housing element designed in this way can be collapsible, for example, with the individual housing parts remaining connected to one another by a film hinge. It is also possible for two individual housing parts to be snapped together via a snap-fit mechanism, for example, the snap fit being releasable. A housing element made up of several parts can make the fitting of the containers or of the drive member and of the rotary member easier, but it is more complicated to produce and requires additional maneuvers for preparing the rotating device.

According to a further aspect of the present invention, a system for discharging and dosing components from containers is provided. The system comprises at least one container that can receive a component and that has an outlet and a discharge element, and a discharge device for driving the discharge element. The discharge device comprises a housing element with a drive member arranged therein or thereon and with a rotary member arranged therein or thereon. The discharge device is removable from the container, or the container is removable from the discharge device. The system preferably comprises two or more containers. The system thus consists of several containers and of a discharge device, which can be mounted as a kind of accessory device onto the containers and can be removed from these again. With the discharge device and containers in the assembled state, the discharge system corresponds to a discharge apparatus as described above. For a user, it is advantageous that the discharge device of the system according to the invention is suitable for discharging from different types of containers. The containers simply have to be inserted into the housing element of the discharge device and can then be emptied by rotation of the rotary member relative to the drive member, with the rotary member acting on the discharge elements in the containers.

As has been described above, the rotary member is for this purpose preferably arranged on the housing element in a rotatable but axially fixed manner. The drive member in turn is received by the housing element in a rotationally fixed but axially movable manner. A threaded connection is provided between the drive member and the rotary member. The rotating device and the housing element can for this purpose be designed in the manner described above.

In an advantageous embodiment of the discharge system according to the invention, the rotating device comprises a set of rotary members, which set consists of rotary members of different thread pitch. Moreover, the rotating device has a set of drive members, which set consists of drive members of different thread pitch. For each rotary member of a defined thread pitch, a drive member with a complementary thread pitch is provided. In order to assemble the discharge device of the system for a defined type of discharging or for a defined container, a suitable pairing of rotary member and drive member can be chosen from the set of rotary members and from the set of drive members, depending on the discharging requirements. If, for example, slow discharging from the containers is to be provided, a pairing of members with a small pitch can be chosen. If rapid discharging is required, a pairing of members with a large thread pitch is chosen. The chosen rotary member and drive member of the pairing of members is then arranged on or in the housing element in order to form, with the latter, the discharge device or accessory device.

In principle, it is of course also possible to provide a set of different housing elements having a suitable guide for the drive members from the set of drive members and a suitable seat for the rotary members from the set of rotary members, but having different container seats for receiving containers of different designs.

The discharge system is thus of modular design, and a suitable discharge device can be assembled depending on the discharging requirements or on the specifications of a defined container. It is advantageous that the discharge device consists of only a few structural parts and can be easily assembled and dismantled.

The present invention forms, among other things, a development of the discharge appliance according to Swiss patent application no. 0038/08 from the applicant, the priority of which document is claimed and to which reference is made in respect of individual features of the discharge apparatus.

The discharge apparatus according to the present invention comprises, in the form of the housing element, a housing for receiving multiple components and, in the form of the rotary member, a rotating part with a thread. The housing element and the rotary member cooperate in such a way that, by rotation of the rotary member, a multiple ram in the form of the drive member acting on the pistons, as the discharge elements, can move continuously in the discharging direction relative to the housing element. The drive member according to the present invention can also be designed as a multiple ram, as is shown, for example, in FIG. 2 of the priority application. The housing element is designed in such a way that it can receive two containers lying next to each other. The thrust force of the rotary member can be transmitted directly to the drive member in the form of the multiple ram, without changing the overall length of the discharge apparatus.

The housing element according to the invention can receive a multiple cartridge, which has at least two containers lying next to each other. According to the present invention, the multiple cartridge is provided on the housing element so as to be removable or replaceable. The rotating part in the form of the rotary member according to the present invention has an inner thread which cooperates with a corresponding outer thread on the drive member in the form of the double ram. Instead of a thread surface extending along the entire length of the drive member, said drive member can for this purpose have an advancer flange, which is provided on its outer area with the outer thread. The connection between the inner thread of the rotary member and the outer thread of the advancer flange causes the drive member to move forward in the axial direction when the rotary member is rotated. In order to secure the drive member against rotation, the advancer flange can be secured against rotation between the guide flanks on the housing element, which form a kind of guide slot.

According to the invention, the housing element, or also a second housing element connected releasably to the first housing element, can receive the multiple cartridge. The housing element with the multiple cartridge can then have an outlet end, which has a bayonet claw reinforcement. This bayonet claw reinforcement can support a bayonet claw provided on the outlets of the multiple cartridge.

The housing element in which the multiple cartridge is accommodated can be made at least partially transparent in the longitudinal direction of the multiple cartridge, such that the discharge element in the interior of the container is visible through the transparent area and can serve as an indicator of the filling level in the container. For this purpose, the housing element can be provided with a graduation which indicates the volume already discharged or the volume still present in the container.

Figure 6:
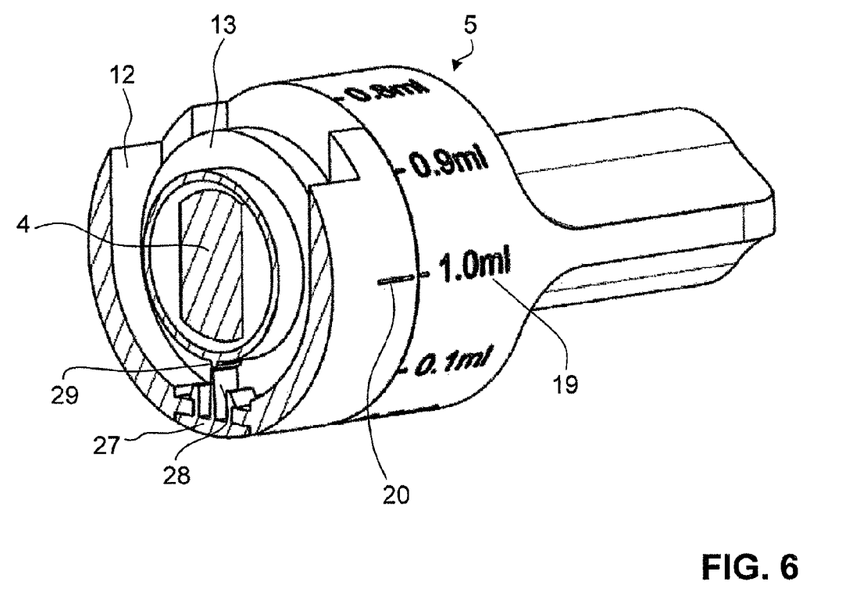
FIG. 6 shows a three-dimensional sectional view through a discharge device according to the present invention.

The discharge apparatus according to the present invention can also have a means which gives an audible signal when the rotary member is turned about a defined angle of rotation, as is outlined in FIG. 6 and in the associated description of the priority document.

BRIEF DESCRIPTION OF THE DRAWINGS

Preferred embodiments of the invention are shown in the drawing, which is not to be seen in any way as limiting the invention. Features of the invention that are disclosed in the figures of the drawing are intended to be understood as belonging to the disclosure. In the drawing.

Figure 1:
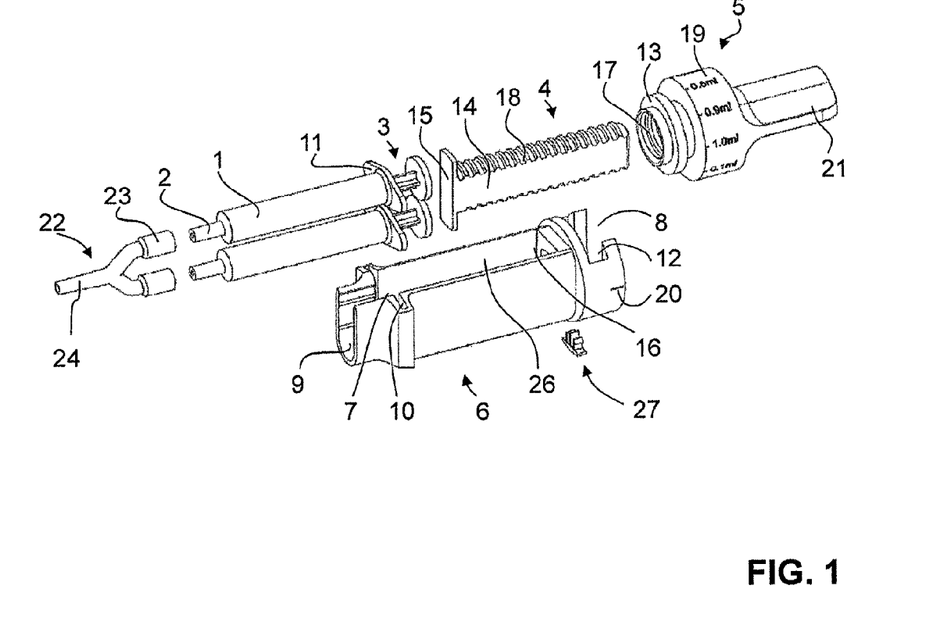
FIG. 1 shows an exploded view of a discharge apparatus according to the present invention.

An exploded view of a discharge apparatus according to the present invention is shown in FIG. 1. In this embodiment, the discharge apparatus comprises two containers 1, each with an outlet 2 and a discharge element in the form of a piston rod 3. In another embodiment according to FIG. 8, the discharge apparatus has only one container. Moreover, the discharge apparatus comprises a rotating device, with a drive member in the form of a threaded rod 4 and with a rotary member 5, and a housing element 6. The housing element 6 has, at one end, a container seat 7 for detachably receiving the containers 1 and, at the other end, a rotary member seat 8 for detachably receiving the rotary member. The housing element 6 is elongate, with the length being oriented in the direction of travel that is required to be able to discharge the complete amount of a component that is accommodated in the container. The housing element 6 is shell-shaped or sleeve-shaped. To allow the piston rod 3 to pass through the housing element, the latter has a passage 9 in the longitudinal direction with a lateral opening 26. To form the container seat 7, retaining depressions in the form of two slits 10, lying opposite each other and perpendicular to the longitudinal axis of the housing element 6, are formed in the circumferential wall of the housing element 6. The slits are open on one side of the housing element and closed on the other side of the housing element. The container 1, at its end remote from the outlet 2, has projections in the form of two wings 11 protruding at right angles from the axis of the container. The wings 11 of the container and the slits 10 of the housing element 6 are dimensioned in such a way that the wings 11 can be inserted on the open side into the slits 10 and, in this way, the container 1 is held in the axial direction relative to the housing element 6. The piston rod 3 thus comes to lie in the passage 9.

For the rotary member seat 8, the housing element 6 has, at the other end, a blind groove 12, which has an insertion opening laterally on the housing element 6. On the opposite side, the groove is closed and designed as an annular groove. The rotary member 5 has a substantially sleeve-shaped design and at one end has, around its circumference, a radially protruding flange 13. The blind groove 12 of the housing element 6 and the flange 13 of the rotary member 5 are dimensioned in such a way that the flange 13 can be inserted into the blind groove 12 and is received rotatably by the latter. In this way, the rotary member 5 is mounted in an axially fixed manner on the housing element 6.

The threaded rod 4 is designed as a flattened rod with two parallel guide surfaces 14 lying opposite each other. At its end lying opposite the containers 1, the threaded rod 4 has a widening plate 15, the surface of which is large enough to be able to engage both of the mutually adjacent piston rods 3 of the two containers 1. The housing element 6 has, in a passage area, two passage flanks 16 that form a through-opening for the threaded rod 4. The flanks 16 extend parallel to each other at a distance corresponding to the thickness of the threaded rod 4 between the guide surfaces 14. When the threaded rod 4 is pushed through the opening between the two flanks 16, the guide surfaces 14 and the flanks 16 come to lie on each other, and the threaded rod 4 is secured against rotation relative to the housing element 6.

The rotary member 5 has, in its inner circumference, an inner thread 17. The inner thread can extend along the entire length of the sleeve-like interior or can be provided only in a starting area. The length of the rotary member 5 is adapted to the length of the threaded rod 4. On its outer circumference between the guide surfaces 14, the threaded rod 4 has an outer thread 18, which corresponds with the inner thread of the rotary member 5.

In a drum-like area of its outer circumference, the rotary member 5 has a rotation scale 19 which assigns a discharged or dosed amount of component to a rotation position of the rotary member. At the end opposite the rotary member 5, the housing element 6 has a pointer 20, which indicates a rotation position of the rotary member relative to the housing element 6.

At its end remote from the housing element 6, the rotary member 5 has grip wings 21 by which the rotary member 5 can be held manually, so as to be able to turn it relative to the housing element 6.

A mixer attachment 22, with two inlet channels 23 that run together to form a common outlet channel 24, is provided on the outlet end of the containers 1.

Figure 2:
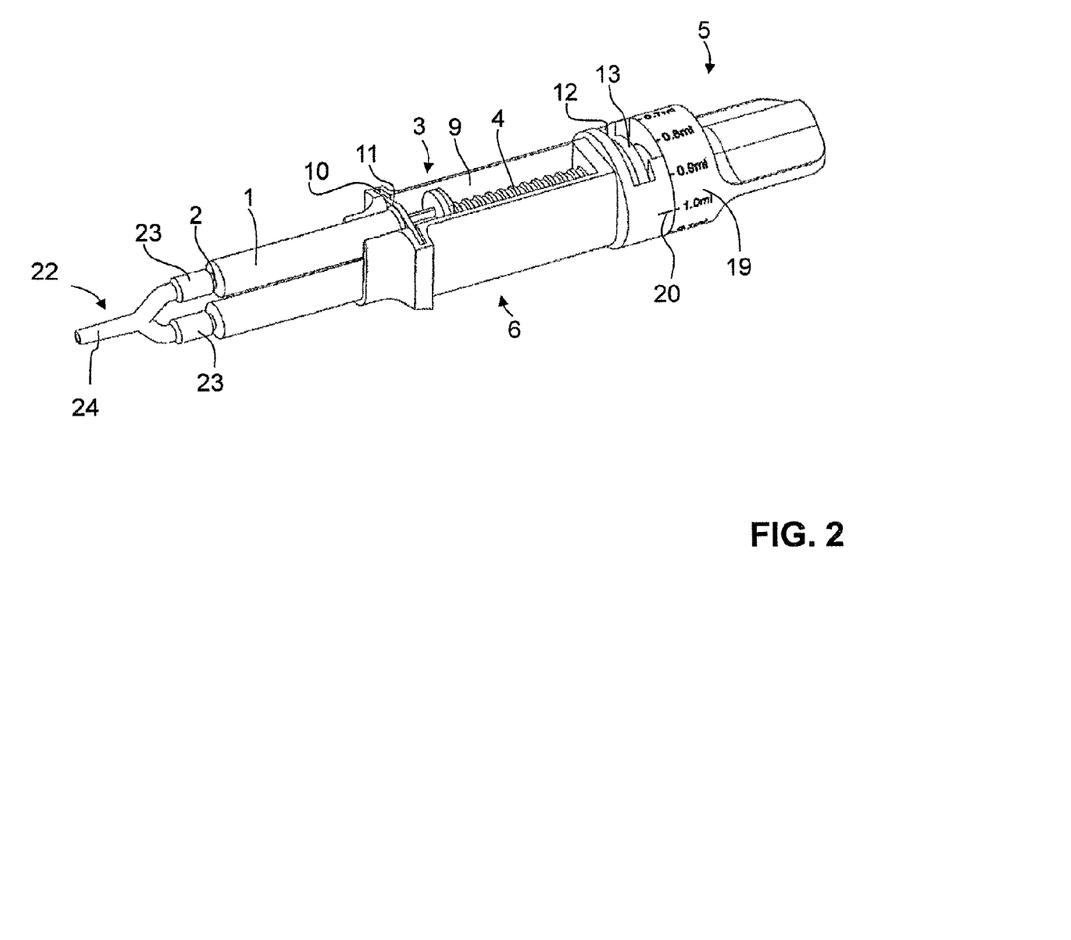
FIG. 2 shows a discharge apparatus according to the present invention in the assembled state.

In FIG. 2, the discharge apparatus from FIG. 1 is shown in the assembled state. The containers 1 are inserted with their wings 11 into the slits 10 of the housing element 6, with the piston rods 3 coming to lie in the laterally open passage 9. The mixer attachment 22 is mounted with the two inlet channels 23 each on a respective outlet 2 of the containers 1. The rotary member 5 is fitted with its flange 13 laterally into the blind groove 12. The rotation scale 19 of the rotary member 5 comes to lie opposite the pointer 20 on the housing element 6. The threaded rod 4 is passed through with its guide surfaces 14 between the flanks 16 of the housing element 6 and extends through the passage 9 and protrudes from the end of the housing element 6 and into the rotary member 5. The inner thread 17 of the rotary member 5 and the outer thread 18 of the threaded rod 4 mesh with each other.

In order to assemble the discharge apparatus according to the present invention, the rotary member 5 is first pushed with the flange 13 into the blind groove 12 of the housing element 6. The threaded rod 4 is then pushed through between the flanks 16 of the housing element 6 until it comes to lie at the start of the inner thread 17 of the rotary member 5. The rotary member 5 is turned inside the blind groove 12 until the inner thread 17 engages in the outer thread 18 of the threaded rod 4 and holds the threaded rod 4 securely. By turning the rotary member further, the threaded rod 4 is screwed into the rotary member, such that space for the piston rods 3 of the containers 1 becomes free in the passage 9. In this assembled state, the housing element 6, the rotary member 5 and the threaded rod 4 form a discharge device or rotating device which, for example, can be supplied as an accessory along with the containers 1. The containers 1 are finally inserted with their wings 11 into the slits 10 of the housing element 6, such that the piston rods 3 lie opposite the widening plate 15 of the threaded rod 4.

Figure 3:
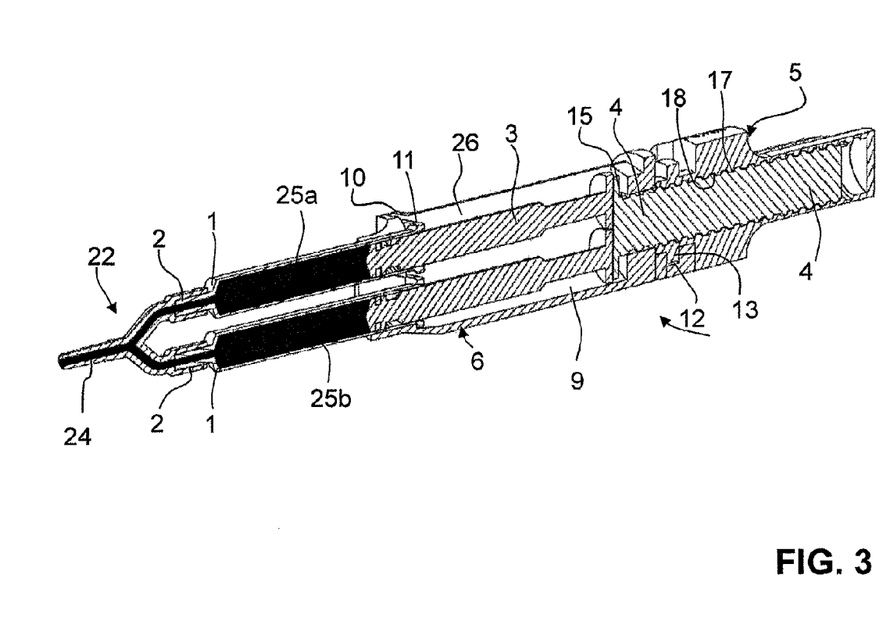
FIG. 3 shows a longitudinal section through a discharge apparatus according to FIG. 2 in an initial state.

FIG. 3 shows a sectional view through a discharge apparatus according to the present invention, in which the discharge apparatus is in an initial state. The containers 1, arranged in parallel one above the other, have been pushed into the slit 10 of the housing element 6. In the interior of the container, a first component 25a can be seen in the first container, and a second component 25b in the second container. The mixer attachment 22 has been fitted onto the two outlets 2 of the containers 1, such that there is a communication of fluid between the containers and the mixer attachment. At the end of the containers 1 remote from the outlet, the piston rods 3 are inserted into said containers in a leaktight manner. The end of the piston rod inserted into the containers thus forms a movable piston or stopper, which provides a tight seal with the inner circumferential wall of the container but is movable. The piston rods 3 come to lie in the passage 9 of the housing element 6. At the opposite end of the containers, the rotary member 5 is inserted into the blind groove 12 of the housing element 6. In so doing, the flange 13 comes to lie in the blind groove 12 and serves as rotation guide for the rotary member 5. The threaded rod 4 is guided through the passage 9 of the housing element 6 and screwed into the rotary member 5. It can be seen how the threaded rod 4 is received with almost its entire length in the interior of the sleeve-shaped rotary member 5. The piston rods 3 come to lie with their end remote from the container on the widening plate 15 of the threaded rod 4. The threaded rod 4 is guided in an axially movable but rotationally fixed manner by the guide means in the form of the flanks 16 of the housing element 6, such that, upon rotation of the rotary member in the blind groove 12 of the housing element, the threaded connection formed by the inner thread 17 on the rotary member 5 and the outer thread 18 on the threaded rod 4 ensures that the rotation movement is converted into a forward movement of the threaded rod 4, such that the widening plate 15 abuts against the end surfaces of the piston rods 3.

It will be seen from FIG. 3 that the passage 9 of the housing element 6 has a lateral slit opening 26 extending in the longitudinal direction. The slit opening extends as far as a wall arranged in the housing element 6, which wall extends transversely with respect to the longitudinal axis of the housing element, and in which wall the flanks 16 are cut out and thus continue the passage 9. The blind groove 12 is likewise open on one side of the housing element and is closed on the opposite side, in which it forms the annular groove for the flange 13, which annular groove guides the rotary member 5 during a rotation.

Figure 4:
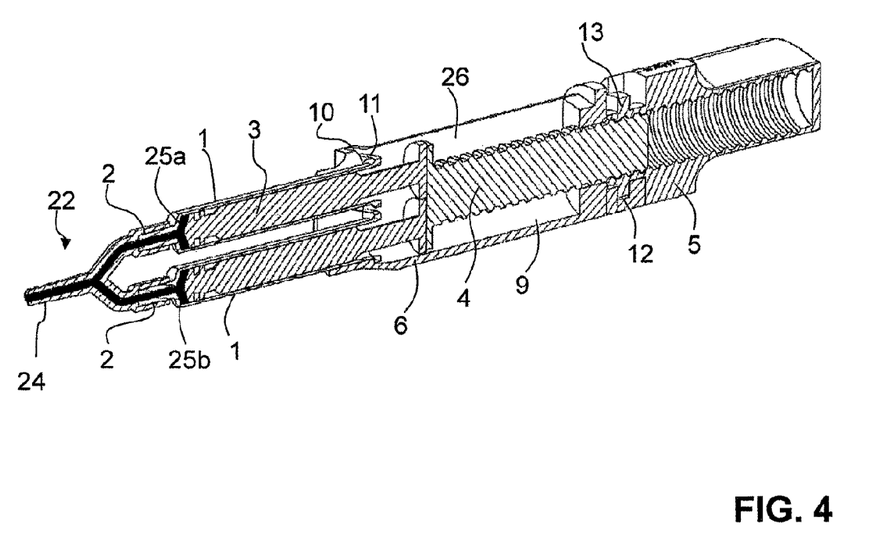
FIG. 4 shows a longitudinal section through a discharge apparatus according to FIG. 2 in an ejection state.

FIG. 4 shows the discharge apparatus in a state in which the components 25a and 25b have been ejected from the containers 1. For this purpose, the rotary member 5 has been rotated relative to the housing element 6, such that the threaded rod 4 moves forward, relative to the housing element 6 and rotary member 5, in the axial direction toward the containers 1 and the piston rods 3. The advancing force of the threaded rod 4 is transferred to the piston rods 3, which are moved forward inside the containers 1 in the direction of the outlets 2, thus forcing the components through the outlets 2 into the channels 23, 24 of the mixer attachment 22. The containers 1 are held securely in the housing element 6 in this process, since their wings 11 abut against the flanks of the slits 10 in the forward direction. The threaded rod 4 is moved through the passage 9 of the housing element 6 between the flanks 16.

FIG. 6 shows a cross section through the discharge apparatus according to the invention, said cross section running through the line along the flange 13 of the blind groove 12 of the housing element 6. In this illustrative embodiment, the flange 13 is provided, on its outer circumference, with a peripheral channel. This results in a kind of two-walled flange, where the channel is located between the mutually opposite inner faces of the walls, and the flange can be inserted with the outer faces of the walls into the annular groove of the blind groove 12 with an exact fit. It will be seen from the sectional view that an acoustic element 27 is inserted into the circumferential wall at the location of the blind groove 12 of the housing element 6, at a place where the blind groove 12 forms the semicircular annular groove. The acoustic element 27 can be snapped with a snap-fit connection into an opening in the housing element 6. The acoustic element 27 has an elastically deflecting leaf or a tongue 28. The tongue protrudes in the radial direction with respect to the center axis of the rotary member 5. A radially outwardly extending projection 29 is provided on the circumferential surface between the two walls of the flange 13. The projection 29 extends in such a way that it deflects the tongue 28 of the acoustic element 27 upon rotation of the rotary member 5. If the rotary member, and thus the projection 29, is rotated further, the tongue 28 snaps over the projection 29 and generates a click sound. It is also possible to arrange, next to the tongue 28, an abutment wall against which the tongue 28 strikes when it snaps back and thus generates a sound. Of course, several projections 29 can be provided on the circumference of the inner face of the flange, and it is also possible to provide several acoustic elements 27 on the housing element 6.

FIG. 6 also shows the rotation scale 19 on the rotary member 5, and the pointer 20 on the housing element 6. The rotation scale 19 consists of volume indicators in tenth of a milliliter steps. When the rotary member 5 is rotated, the rotation scale 19 is turned relative to the pointer 20 and thus indicates the amount of the components discharged from the containers.

Figure 5A:
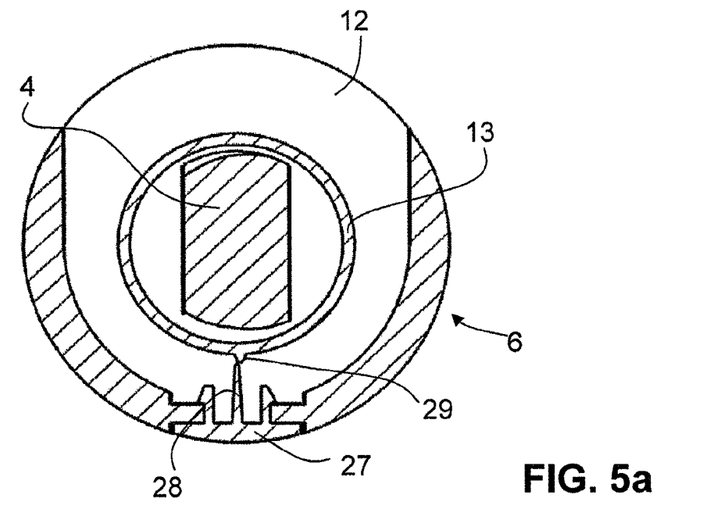
FIG. 5a shows a transverse section through a discharge apparatus according to the present invention, with a flexible tongue in the undeflected state.
Figure 5B:
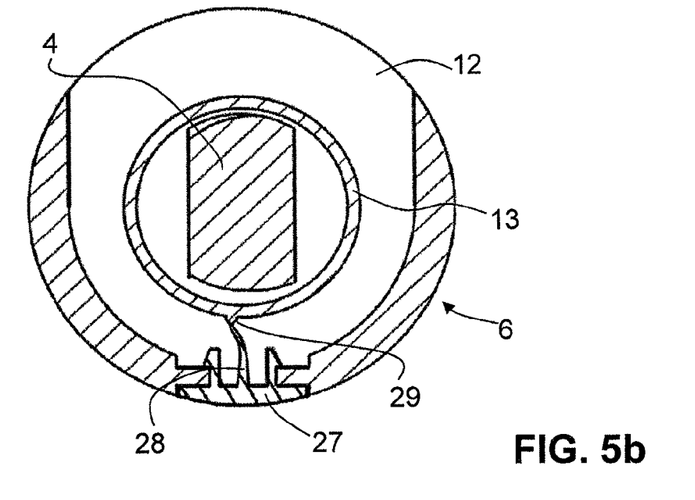
FIG. 5b shows a transverse section through a discharge apparatus according to FIG. 5a, with a deflected flexible tongue.

FIGS. 5a and 5b show a front view of the cross section from FIG. 6. In FIG. 5a, the projection 29 on the flange 13 of the rotary member 5 comes to lie exactly on the tongue 28 of the acoustic element 27 in the circumference of the housing element 6. In FIG. 5b, the rotary member 5, and thus also the flange 13 with the projection 29, has been moved clockwise relative to the housing element 6, such that the projection 29 deflects the tongue 28 of the acoustic element 27. As soon as the rotary member is turned further in the clockwise direction, the tongue 28 slips away from the projection 29 and generates an acoustic signal. As long as the projection 29 engages on the tongue 28, the rotation movement of the rotary member 5 is braked gently but perceptibly. By means of this braking action, a tactile signal is provided for a defined rotation position.

Figure 7:
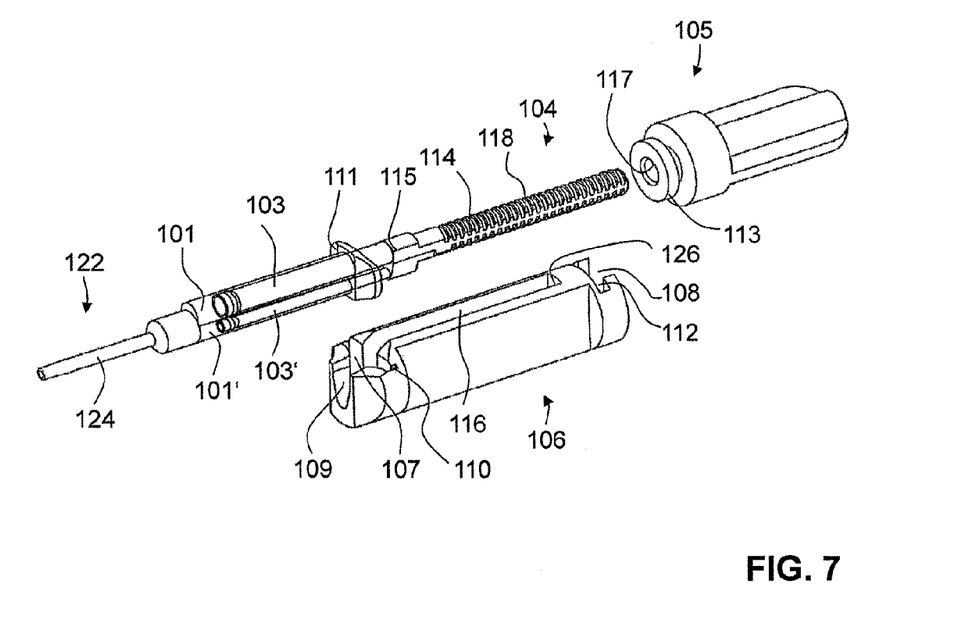
FIG. 7 shows an exploded view of another embodiment of a discharge apparatus according to the present invention.

FIG. 7 shows another embodiment of a discharge apparatus according to the present invention. Two containers 101 and 101' have been chosen from a system according to the invention for discharging and dosing components from containers. The containers 101 and 101' are sleeve-shaped, the container 101' having a smaller diameter than the container 101. The containers 101 and 101' are of the same length. At one end of the containers, outlets are provided onto which a mixer attachment 122 with an outlet channel 124 is fitted. At the other end, the containers 101 and 101' are closed with movable pistons on piston rods 103 and 103'. The piston rods 103 and 103' are adapted to the respective diameter of the containers 101 and 101'. The containers 101 and 101' have common wings 111, which protrude from the containers at right angles to the longitudinal axis.

A discharge apparatus for driving the discharge elements of the containers in the form of piston rods 103 and 103' has a housing element 106. A drive member in the form of a threaded rod 104 is also provided, which is to be arranged in the housing element 106. The discharge apparatus further comprises a rotary member 105, which is likewise to be arranged on the housing element 106. The threaded rod 104, the rotary member 105 and the housing element 106 together form the discharge device. At one end of the housing element 106, a container seat 107 is provided, into which the containers 101 and 101' can be inserted and from which they can be removed again for replacement of the containers.

The rotary member 105 has been chosen from a set of rotary members, which set comprises rotary members with different thread pitches. Such a set of rotary members can consist of several rotary members, for example the rotary member 5 and the rotary member 105. The individual rotary members differ from one another in terms of the pitch of their inner threads, for example the inner threads 17 and 117. The drive member has been chosen from a set of drive members, which set consists of drive members with different thread pitch. The set of drive members can comprise several drive members, for example the threaded rods 4 and 104, which differ from one another in terms of, among other things, the pitch of their outer threads 18 and 118. The threaded rod 104 and the rotary member 105 were chosen according to the requirements for the dosing and discharging of the components from the containers 101 and 101', and they are inserted into the housing element 106, with which they together form a discharge device or rotating device.

The housing element 106 has a slit 110 into which the wings 111 of the containers can be inserted, as in the illustrative embodiment according to FIGS. 1 to 6. The housing element also has a passage 109 and a lateral longitudinal opening 126, through which the threaded rod 104 can be inserted into the housing element 106. In the interior of the housing element 106, the longitudinal opening 126 and the passage 109 have flanks 116, which extend in parallel along almost the entire length of the housing element 106 and which serve as guide means for the threaded rod 104. At the end opposite the container seat 107, the housing element 106 has a rotary member seat 108. The rotary member seat 108 is designed as a blind groove 112, comparable to the configuration of the container seat 7 in FIGS. 1 to 6.

The threaded rod 104 has lateral guide surfaces 114 along its length, which guide surfaces 114 are less wide than the guide surfaces 14 of the threaded rod 4, such that the circumferential surface for the outer thread 118 on the threaded rod 104 is greater. At the end that engages on the piston rods 103 and 103' of the containers 101 and 101', the piston rod has a widening plate 115 which, along its widening, has surfaces extending parallel to the guide surfaces 114 and merging into these. In a state in which the threaded rod 104 is inserted into the housing element 106, the guide surfaces 114, which extend along the entire length of the threaded rod 104, come to lie on the flanks 116 of the housing element 106, such that the threaded rod 104 is secured against rotation along the entire length of the housing element 106. As in the preceding illustrative embodiment according to FIGS. 1 to 6, the threaded rod 104 is guided through the passage 109 as far as the rotary member 105, which is fitted with its flange 113 into the blind groove 112. By a rotation of the rotary member 105 relative to the housing element 106, the threaded rod 104 is received with its outer thread 118 by the inner thread 117 of the rotary member 105.

For administering the components from the containers 101 and 101', the rotary member 105 is rotated, whereupon the threaded rod 104 is advanced forward inside the housing element 106 and transfers the advancing force to the piston rods 103 and 103'. The piston rods 103 and 103' are moved in parallel and at the same speed within the respective containers. Because of the different diameters of the containers, a different amount of the components is discharged from the respective containers in accordance with a proposed dosage.

The embodiment according to FIG. 7 shows that the system for discharging components from containers is suitable for meeting different requirements concerning the discharging of components. A suitable drive member and a suitable rotary member can be chosen for the discharge device or rotating device. The elements of the system are then combined to form a discharge apparatus.

Figure 8:
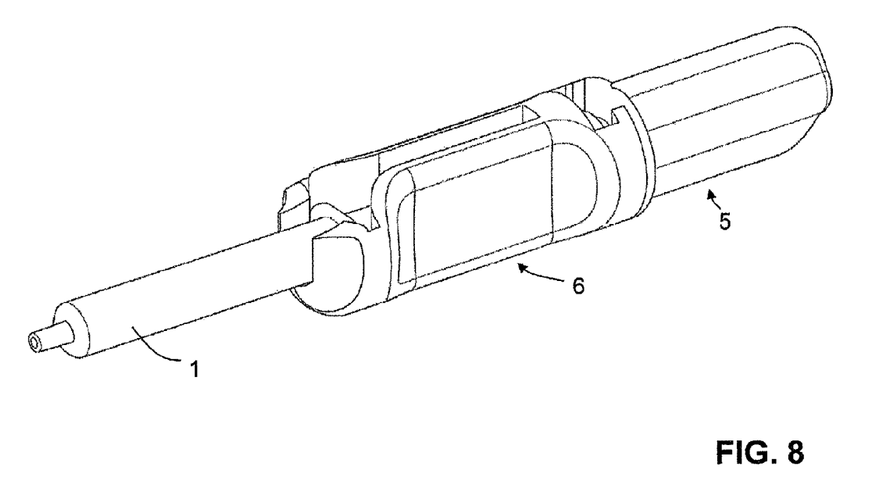
FIG. 8 shows a three-dimensional view of another embodiment of a discharge apparatus according to the present invention with only one container.

FIG. 8 shows another embodiment of the present invention in which the discharge apparatus comprises only one container 1. The container 1 and the rotary member 5 are inserted into the housing element 6. The mode of function of this embodiment corresponds to the use described in the preceding illustrative embodiments. Even with discharging from just one container, the accessory is able to ensure simple and exact dosing.

LIST OF REFERENCE SIGNS 1 container
2 outlet
3 piston rod/discharge element
4 threaded rod/drive member
5 rotary member
6 housing element
7 container seat
8 rotary member seat
9 passage
10 slit
11 wing
12 blind groove
13 flange
14 guide surface
15 widening plate
16 flank
17 inner thread
18 outer thread
19 rotation scale
20 pointer
21 grip wing
22 mixer attachment
23 inlet channel
24 outlet channel
25a,b components
26 longitudinal opening
27 acoustic element
28 tongue
29 projection
101 container
101' container
103 piston rod
103' piston rod
104 threaded rod
105 rotary member
106 housing element
107 container seat
108 rotary member seat
109 passage
110 slit
111 wing
112 blind groove
113 flange
114 guide surface
115 widening plate
116 flanks
117 inner thread
118 outer thread
122 mixer attachment
124 outlet channel
126 longitudinal opening

The invention claimed is:

1. A discharge apparatus for discharging at least one component from at least one container, the container having an outlet and a discharge element in the form of a piston rod, the apparatus comprising:
    an elongate and sleeve-shaped housing element to removably receive the at least one container, the housing element defining a longitudinal passage to allow the discharge element to pass through the housing element, the passage having a lateral opening;
    a drive member in the form of a threaded rod, the threaded rod to engage on the discharge element of the at least one container, the threaded rod being axially movable along an axial direction and rotationally fixed relative to the housing element; and
    a rotary member disposed on or in the housing element in a manner to be rotatable and axially fixed relative to the housing element, the rotary member cooperating with the drive member via a threaded connection such that a rotation of the rotary member relative to the drive member causes the drive member to move axially relative to the housing element so as to drive the discharge element of the at least one container for discharging the at least one component,
    wherein the housing element has, at a first end, a container seat for detachably receiving the at least one container and, at a second end, a rotary member seat for detachably receiving the rotary member.

2. The discharge apparatus as claimed in claim 1, wherein the at least one container is a syringe having a sleeve-shaped body with a first and a second end, the outlet being provided at the first end, the body being closed at the second end by a movable piston, and wherein the discharge element is a piston rod for pushing the movable piston forward.

3. The discharge apparatus as claimed in claim 1, the apparatus being adapted to receive two or more containers.

4. The discharge apparatus as claimed in claim 3, wherein the containers are syringes arranged in parallel, each syringe having a sleeve-shaped body with a first and a second end, the outlet being provided at the first end, the body being closed at the second end by a movable piston, and wherein the discharge element of each syringe is a piston rod for pushing the movable piston forward.

5. The discharge apparatus as claimed in claim 1 wherein at least one of the drive member and the rotary member is mounted removably on or in the housing element.

6. The discharge apparatus as claimed in claim 1, wherein the threaded connection is provided directly between the rotary member and the drive member.

7. The discharge apparatus as claimed in claim 1, wherein the threaded rod has an outer thread and is flattened on two opposite longitudinal sides so as to form two parallel guide surfaces spaced by a thickness of the threaded rod between the guide surfaces, the guide surfaces interrupting the outer thread to form thread segments, and wherein the housing element has two mutually parallel flanks having a distance corresponding to the thickness of the threaded rod between the guide surfaces, the flanks abutting to the guide surfaces in such a way that the threaded rod is axially movable and rotationally fixed in relation to the housing element.

8. The discharge apparatus as claimed in claim 1, wherein the threaded rod has an outer thread, and wherein the rotary member is sleeve-shaped and has, on its inner circumference, an inner thread cooperating with the outer thread of the threaded rod.

9. The discharge apparatus as claimed in claim 1, wherein the rotary member protrudes from the housing element by an amount sufficient for the rotary member to be gripped manually and rotated relative to the housing element.

10. The discharge apparatus as claimed in claim 1, wherein the rotary member, at an end remote from the housing element, has grip wings so as to hold the rotary member manually and to turn the rotary member relative to the housing element.

11. The discharge apparatus as claimed in claim 1, wherein the rotary member has a rotation scale along its circumferential direction, and the housing element has a pointer lying opposite the rotation scale.

12. The discharge apparatus as claimed in claim 1, wherein the rotary member is adapted to be fitted laterally to the housing element.

13. The discharge apparatus as claimed in claim 1, wherein the housing element has an annular groove extending around at least part of its circumference, and the rotary member has a flange that is adapted to be laterally inserted into the annular groove.

14. The discharge apparatus as claimed in claim 13, wherein the annular groove extends through approximately 180° about the circumference of the housing element.

15. The discharge apparatus as claimed in claim 1, wherein an acoustic device is provided for generating an acoustic signal upon rotation of the rotary member.

16. The discharge apparatus as claimed in claim 15, wherein the acoustic device comprises a flexible tongue cooperating with at least one projection, one of the tongue and the projection being mounted on the housing element and the other one of the tongue and the projection being mounted on the rotary member in a manner that the projection deflects the tongue upon rotation of the rotary member.

17. The discharge apparatus as claimed in claim 1, wherein the housing element has a laterally open retaining depression to removably receive a projection on the container for securing the container on the housing element.

18. The discharge apparatus as claimed in claim 1, wherein the housing element has two opposite slits formed in a wall of the housing element, the slits extending perpendicular to the axial direction, the slits being open to one side of the housing element to laterally receive wings protruding at right angles from the container, for holding the container axially relative to the housing element.

19. A system for discharging components from containers, comprising:
at least one container that receives a component and that has an outlet and a discharge element, and
a discharge apparatus for driving the discharge element, which discharge apparatus comprises a housing element, a set of rotary members to be arranged in or on the housing element, which set of rotary members consists of rotary members of different thread pitch, and a set of drive members to be arranged in or on the housing element, which set consists of drive members of different thread pitch,
the discharge apparatus being removable from the container.

20. The system as claimed in claim 19, wherein the housing element is adapted to receive one of the rotary members in a rotatable and axially fixed manner and to receive one of the drive members in a rotationally fixed and axially movable manner, with a threaded connection being provided between the drive member and the corresponding rotary member such that a rotation of the rotary member relative to the drive member causes the drive member to move axially relative to the housing element so as to drive the discharge element of the at least one container for discharging the component.

21. A discharge apparatus for discharging at least one component from at least one container, the container having an outlet and a discharge element, the apparatus comprising:
a housing element to removably receive the at least one container;
a drive member in the form of a threaded rod, the threaded rod to engage on the discharge element of the at least one container, the threaded rod being axially movable along an axial direction and rotationally fixed relative to the housing element; and
a rotary member disposed on or in the housing element in a manner to be rotatable and axially fixed relative to the housing element, the rotary member cooperating with the drive member via a threaded connection such that a rotation of the rotary member relative to the drive member causes the drive member to move axially relative to the housing element so as to drive the discharge element of the at least one container for discharging the at least one component,
wherein the housing element has an annular groove extending around at least part of its circumference, and the rotary member has a flange that is adapted to be laterally inserted into the annular groove.

22. The discharge apparatus as claimed in claim 21, wherein the annular groove extends through approximately 180° about the circumference of the housing element.

23. The discharge apparatus as claimed in claim 21, wherein the threaded rod has an outer thread, and wherein the rotary member is sleeve-shaped and has, on its inner circumference, an inner thread cooperating with the outer thread of the threaded rod.

24. The discharge apparatus as claimed in claim 21, wherein the housing element has two opposite slits formed in a wall of the housing element, the slits extending perpendicular to the axial direction, the slits being open to one side of the housing element to laterally receive wings protruding at right angles from the container, for holding the container axially relative to the housing element.

* * * * *